United States Patent [19]

Belcour et al.

[11] Patent Number: 4,963,480
[45] Date of Patent: Oct. 16, 1990

[54] PROCESS FOR THE PREPARATION OF GAMMA-IRONE

[75] Inventors: Beatrice Belcour; Didier Courtois, both of Tours; Charles Ehret, Peymeinade, all of France

[73] Assignee: Roure S.A., Argenteuil, France

[21] Appl. No.: 384,415

[22] Filed: Jul. 24, 1989

[30] Foreign Application Priority Data

Aug. 5, 1988 [EP] European Pat. Off. ............ 88810537

[51] Int. Cl.$^5$ .................. C12P 39/00; C12P 7/26; C12R 1/01; C12R 1/38
[52] U.S. Cl. .................................. 435/42; 435/148; 435/240.54; 435/803; 435/822; 435/849; 435/874; 435/880
[58] Field of Search .................................. 435/42, 148

[56] References Cited

U.S. PATENT DOCUMENTS 4,390,557 6/1983 Krasnobajew .................. 435/148

FOREIGN PATENT DOCUMENTS 0107482 9/1978 Japan .................. 435/148

OTHER PUBLICATIONS

Rautenstrauch et al., *Helv. Chim. Acta.*, 54 1776 (1971).
Jaenicke et al., Progress in the Chemistry of Natural Organic Products, 50 1-25 (1986).
Krick et al., Z. Naturforsch. 38C, 179-184 (1983).
Parfums, Cosmetiques, Aromes 77, 49-51 (1987).

*Primary Examiner*—Herbert J. Lilling
*Attorney, Agent, or Firm*—Richard R. Muccino

[57] ABSTRACT

This invention pertains to an improved process for the preparation of gamma-irone by bioconversion comprising treating an iris rhizome substrate selected from the group consisting of iris rhizomes, iris rhizome parts, iris rhizome extracts, iris rhizome extraction wastes, plant cell cultures of iris rhizomes, and mixtures thereof, with a bacteria selected from the genera group consisting of Enterobacteriacea, Pseudomonacea, the active enzyme fractions of such bacteria, and mixtures thereof, in the presence of a plant cell culture medium.

20 Claims, 1 Drawing Sheet

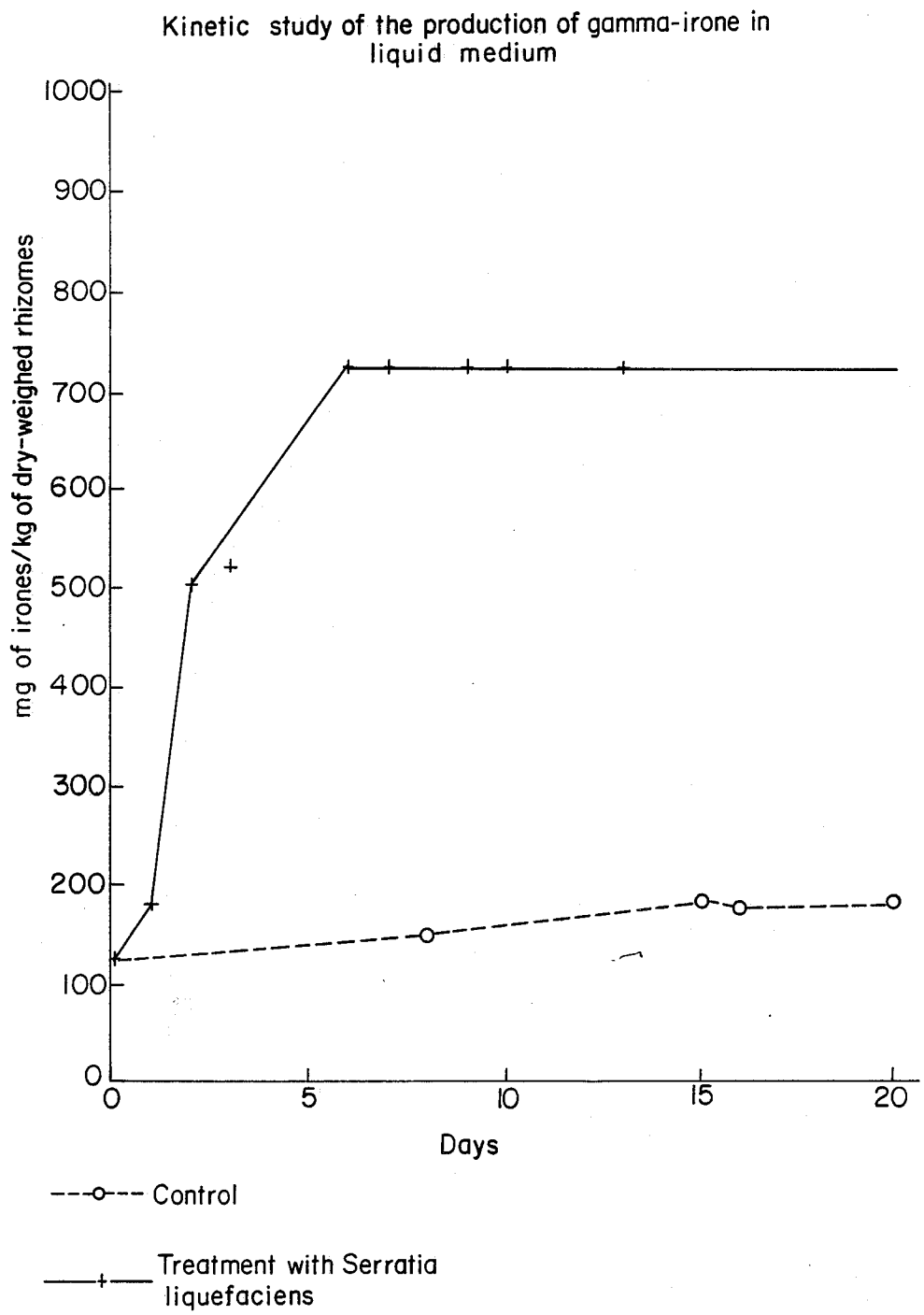
FIG. I

PROCESS FOR THE PREPARATION OF GAMMA-IRONE

BACKGROUND OF THE INVENTION

1. Field of the Invention

This invention pertains to a bioconversion process for preparing gamma-irone.

2. Description of the Prior Art

Rautenstrauch et al., *Helv. Chim. Acta* 54 1776 (1971), The Stereochemistry of Irones, disclose the stereochemical configuration of the irone isomers.

Jaenicke et al., *Progress in the Chemistry of Natural Organic Products*, The Irones and Their Precursors, 50, 1-25 (1986), disclose the formation of irones from the rootstocks of iris rhizomes.

Krick et al., *Z. Naturforsch.* 38C, 179-184 (1983), Isolation and Structure Determination of the Precursors of alpha- and gamma-Irone and Homologous Compounds from *Iris pallida* and *Iris florentina*, disclose that irones are formed by oxidative degradation.

An article in Parfums, cosmetiques, aromes, 77, 49-51 (October 1987) discloses that irones are obtained from fresh iris rhizomes.

SUMMARY OF THE INVENTION

This invention pertains to an improved process for the preparation of gamma-irone by bioconversion comprising treating an iris rhizome substrate selected from the group consisting of iris rhizomes, iris rhizome parts, iris rhizome extracts, iris rhizome extraction wastes, plant cell cultures of iris rhizomes, and mixtures thereof, with a bacteria, said bacteria preferably being selected from the genera group consisting of Enterobacteriacea, Pseudomonacea, the active enzyme fractions of such bacteria, and mixtures thereof, in the presence of a plant cell culture medium.

BRIEF DESCRIPTION OF THE DRAWING

FIG. 1 depicts in graphic format a kinetic study of the production of gamma-irone by treatment of iris rhizomes with a culture of Serratia liquefaciens in a liquid plant cell medium (Example 2).

DETAILED DESCRIPTION OF THE INVENTION

This invention pertains to an improved process for the preparation of gamma-irone by bioconversion comprising treating an iris rhizome substrate selected from the group consisting of iris rhizomes, iris rhizome parts, iris rhizome extracts, iris rhizome extraction wastes, plant cell cultures of iris rhizomes, and mixtures thereof, with a bacteria, said bacteria preferably being selected from the genera group consisting of Enterobacteriacea, Pseudomonacea, the active enzyme fractions of such bacteria, and mixtures thereof, in the presence of a plant cell culture medium.

More specifically, the present invention pertains to an improved process for the preparation of cis-gamma-irone (4-(2,2,3-trimethyl-6-methylenecyclohexyl-3-buten-2-one) as depicted in Formula (3) below. Cis-gamma-irone (3) may be accompanied in the reaction product of the present process by one or more of the irone isomers depicted in Formulae (1) (cis-alpha-irone), (2) (trans-alpha-irone) and (4) (beta-irone) set out below.

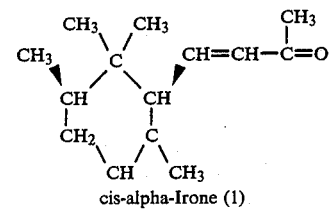
cis-alpha-Irone (1)

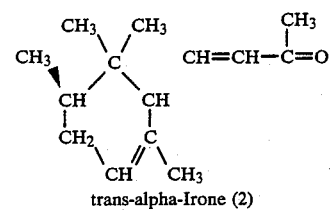
trans-alpha-Irone (2)

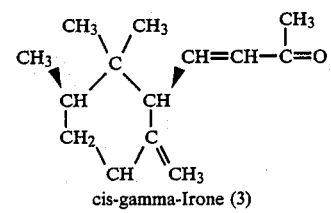
cis-gamma-Irone (3)

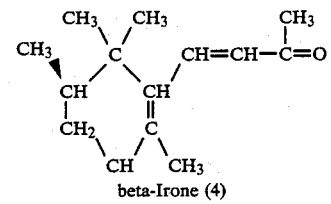
beta-Irone (4)

The bacterial strains of primary interest in the present invention are preferably selected from the genera group consisting of Enterobacteriacea, Pseudomonacea, the active enzyme fractions of such bacteria, and mixtures thereof. The bacteria are preferably isolated from iris rhizomes. Preferred species of bacteria are the following:

Serratia liquefaciens;
Enterobacter cloacae;
Escherichia coli;
Pseudomonas fluorescens; and
Pseudomonas maltophilia:

including the active enzyme fractions of such bacteria, and mixtures thereof.

As pointed out above, the suitable strains of bacteria are preferably isolated from iris rhizomes. These rhizomes are preferably first pretreated, i.e., cleaned, peeled, decontaminated, reduced to small pieces and placed in a nutrient broth, then incubated in order to allow the bacteria to grow, the grown strains isolated, e.g., by the conventional dilution method, purified and identified, e.g., by biochemical test strips. A suitable nutrient broth for bacterial growth may contain:

(i) peptone;
(ii) meat extract;
(iii) yeast extract; and
(iv) inorganic salts, e.g., sodium chloride, ammonium nitrate, etc.

Convenient media for the treatment of the rhizomes with the bacteria and a culture of these bacteria respectively according to the present invention are the conventional, standard media used for the growth of plant callus and suspension cultures. The media thus may contain:
(i) major inorganic nutrients;
(ii) trace elements;
(iii) an iron source;
(iv) organic supplements (vitamins);
(v) a carbon source; and
(vi) organic supplements (plant growth regulators); and may be supplemented by additional nutrient broth, such as that outlined above, for achieving the bacterial growth.

More particularly, these media for the treatment of the rhizomes with the bacteria may be semi-solid or liquid, see for example; S.S. Bhojwani and M. K. Razdaw, Plant Tissue culture: Theory and Practice, Elsevier (1983), e.g., 21 et seq.; and R. A. Dixon, Plant Cell Culture, A Practical Approach, e.g., 2 et seq., IRL Press, Oxford, Washington DC (1985).

Particularly suitable plant cell culture media are the following: Murashige and Skoog, Gamborg, modified Heller, and modified Skoog, and mixtures thereof. In a preferred embodiment, the plant cell culture media is used in the presence of a nutrient broth.

The iris rhizome substrate of the present invention is preferably obtained from an iris plant selected from the group consisting of *Iris pallida*, *Iris florentina*, *Iris germanica*, Iris of Verona, and mixtures thereof.

The iris rhizome substrate, which is preferably taken from the plant in a vegetative state, may be used fresh, i.e., shortly after harvest, in the form of:
iris rhizomes, crushed or powdered,
iris rhizome parts,
iris rhizome extracts, e.g., preferably alcoholic, and more preferably methanolic, extracts,
iris rhizome wastes, i.e., the residues recovered after the industrial extraction of iris rhizomes, and
plant cell cultures of iris rhizomes, and mixtures thereof. In the case of plant cell cultures of iris rhizomes, the iris callus culture may be initiated from an explant on conventional culture media (as listed above) using standard procedures, and the so-obtained plant cells are finally combined with a culture of the microorganism. The iris rhizome substrates are, as outlined above, suitably pretreated.

A suitable temperature range for the process of the present invention is ambient temperature, preferably from about 15° C. to about 40° C., and more preferably from about 25° C. to about 35° C.

A suitable reaction time for the process is from about 1 to about 20 days, with about 3 to about 6 days being preferred.

A suitable range of the ratio by weight of iris rhizome substrate to medium is from about 1:20 to about 2:1, with about 1:10 to about 1:1 being preferred.

In the case where the plant cell culture medium is supplemented by a nutrient broth, a reasonable ratio of plant cell culture medium to total medium (i.e., plant cell culture medium and nutrient broth) is from about 0.5:1 to about 0.95:1.

For a semi-solid medium, a solidifying agent, preferably agar, is added at a final concentration of about 6–15g/liter, with about 8–12g/liter being preferred.

The isolation of the final product is conveniently carried out by the conventional methods as used nowadays for the isolation of the volatiles from plants or for the production of fragrances and flavors, i.e., steam distillation, extraction or the Likens-Nickerson technique involving simultaneous steam distillation and extraction using any suitable volatile organic solvent, preferably methylene chloride, diethyl ether, hexane, and the like, and mixtures thereof.

Naturally, the process may also be conducted in bioreactors, e.g., batch cultures or continuous cultures. In all of these cases, conventional methods of fermentation may be applied including the use of separated phase cultures.

Instead of using bacteria, one can also use the active enzyme fractions obtained therefrom. Such active enzyme fractions are obtained in the usual manner by preparing aqueous extracts of the bacteria and, if desired, cleaning such extracts, e.g., by chromatographic methods, such as ion exchange chromatography, liquid chromatography, gel filtration (preferred), gel electrophoresis, affinity chromatography, and the like. One method which works conveniently is chromatography in buffered solutions, e.g., between pH 5.5 and 6.5. Very often, cleaning is not necessary, and the crude extract can be used directly.

Separation of gamma-irone from the other irone isomers is usually not required. If necessary, such separation can however be accomplished in the usual way, e.g., by chromatographic techniques such as that disclosed in Y. Rautenstrauch and G. Ohloff, *Helv. Chim. Acta*, 54(7) 189 (1971), which disclosure is incorporated herein by reference.

The present invention is further illustrated by the following Examples which are not intended to limit the effective scope of the claims. All parts and percentages in the Examples and throughout the specification and claims are by weight of the final composition unless otherwise specified.

EXAMPLE 1

Production of gamma-irone by treatment of iris rhizomes with a culture of Serratia liquefaciens on a semi-solid medium.

Rhizomes of Iris pallida are taken from a plant in the vegetative state. They are first cleared from excess earth and peeled in order to remove the outer epiderm. Afterwards they are decontaminated by immersion, first in an aqueous alcoholic solution (70% ethanol/30% water by volume) for 30 seconds, then in an aqueous solution of mercuric chloride ($HgCl_2$) (1g/liter) for 30 seconds and finally by rinsing them three times in distilled water. [Another even more simple means of decontamination is autoclaving the rhizomes at 120° C. for 20 minutes].

The decontaminated rhizomes (5g) are cut into small pieces of about 0.5g and plated on the surface of a semi-solid Murashige and Skoog medium (Agar: 10g/liter) (note 1) which medium had previously been inoculated by puncture with the bacterial suspension of Serratia liquefaciens (note 2). As the control experiment, a noninoculated (i.e., non-inoculated with bacteria) solid Murashige and Skoog medium is used under otherwise identical conditions. The incubation is carried out at 30° C. for 15 days. At the end of this period, the rhizomes and the corresponding medium are extracted, together or separately, (i.e., by separating the rhizome parts such as by filtration on a nylon cloth, pore size 50mm), and by simultaneous distillation and extraction (Likens-Nickerson technique, note 3). The combined extracts (extracted rhizomes and medium), as analyzed by gas chromatography (GC) and gas chromatography-mass spectrometry (GC/MS) (note 4), show the following approximate results: trans-alpha-irone 5.4%, cis-alpha-irone 33%, cis-gamma-irone 61%, and unidentifiable 0.6% (assuming the total amount of the irones to be 100%). When compared with the control experiment (2.8 mg/g in the combined extracts/g of fresh rhizomes used as substrate), the amount of cis-gamma-irone (67 mg/g fresh rhizomes), the major natural isomer, produced by the treatment of fresh rhizomes with Serratia liquefaciens has thus been increased by a factor of 24.

Note 1:

Murashige and Skoog medium (T. Murashige and F. Skoog Physiologia Plantarum 15, 473 (1962)) supplemented with 1 mg/liter of 6-furfurylaminopurine (kinetin) and 1 mg/liter of 2,4-dichlorophenoxyacetic acid; 12ml of medium and 0.5g of iris rhizome per test tube.

Note 2:

Isolation and identification of the bacteria Serratia liquefaciens. A rhizome of Iris pallida is cleared from excess earth, peeled and decontaminated (30 seconds in an aqueous alcoholic solution, 70% ethanol/30% water by volume). An internal fragment of about 0.5g of this rhizome, placed in 10ml of nutrient broth (peptone 5g, meat extract 1g, yeast extract 2g, sodium chloride 5g, and water 1 liter), is incubated at 27° C. during 15 days. From this culture the bacterium Serratia liquefaciens is isolated and purified on a Petri dish containing nutrient Agar of similar composition (Agar:10g/liter), and identified by biochemical test strips API 20E/API SYSTEM S.A., 38390 Montalieu-Vercieu, France. The strain is maintained by a weekly transfer on Petri dishes containing nutrient Agar and can be preserved by any standard method.

Note 3:

Likens-Nickerson technique following the procedure described by T. H. Schultz et al., *J. Agric. Food Chem.* 25, 446 (1977) using a volatile solvent, preferably methylene chloride.

Note 4:

Gas chromatography: DELSI DI 700, capillary column Carb. 20M, vector gas 4.5ml/minute Helium, programmation 70/180° C. 2° C./minute. Mass Spectrometer: FINNIGAN 4500, electronic impact.

EXAMPLE 2

Production of gamma-irone by treatment of iris rhizomes With a culture of Serratia liquefaciens in a liquid medium.

For these experiments, three different types of rhizomes have been used:

Batch I: fresh rhizomes in a vegetative state, cleared from excess earth, peeled and cut into small pieces as described in Example 1.

Batch II: dry unpeeled rhizomes harvested in Italy in August 1987, stored at 4° C. before utilization (3-6 months), then powdered just before use.

Batch III: dry unpeeled rhizomes, matured for 3 years at room temperature and several months at 45° C. and then treated as above (batch II).

a) Experiments with the Murashige and Skoog medium.

The powdered and cut rhizomes respectively are sterilized in 250ml Erlenmeyer flasks (5g rhizomes per flask) by autoclaving at 120° C. during 30 minutes. After cooling, 100ml of Murashige and Skoog medium and 10ml of nutrient broth (see Example 1 and Note 5) are added to each flask under sterile conditions. With the exception of the control experiments, each of the flasks is inoculated with 0.5ml of a 24 hours old culture (nutrient broth, 25° C., gyratory shaker) of Serratia liquefaciens (see Example 1 for the isolation) and incubated on a gyratory shaker (100 revolutions/minute) at 25° C. during two weeks (Note 6). At the end of this period, both the rhizomes and the medium are extracted and analyzed as described in Example 1.

The results (batch I, II, and III) expressed in mg of irones/kg of dry-weighed rhizomes are given in Table I. The average distribution of irones in these extracts is the following:

trans-alpha-irone 6.5%,
cis-alpha-irone 34%,
cis-gamma-irone 58%,
beta-irone 1.5%, and
unidentifiable irone(s) 0.2%.

In contradistinction thereto, the classical Likens-Nickerson extraction (without microbiological treatment) of mature rhizomes (batch III) yields 700 mg of irones/kg of dry-weighed rhizomes exhibiting approximately the following distribution:

trans-alpha-irone 4%,
cis-alpha-irone 44%,
cis-gamma-irone 50%,
beta-irone 1.2%, and
unidentifiable irone(s) 0.8%.

TABLE I

|  | Batch I | Batch II | Batch III |
|---|---|---|---|
| (T) Treatment with Serratia liquefaciens | 720 | 675 | 822 |
| (C) Control experiment | 68 | 198 | 623 |
| (R) = T/C | 10.5 | 3.5 | 1.3 |

Note 5:

Under normal conditions of bacterial growth, the treatment of iris rhizomes with Serratia liquefaciens by using a nutrient broth only (i.e., a conventional nutrient broth for the bacterial growth) does not lead to any increase of the content of irones.

Note 6:

A kinetic study has shown that for batch I the maximum content (720 mg of irones/kg of dry-weighed rhizomes) was obtained after 5 days of incubation. The results of the kinetic study are set out in FIG. 1.

b) Experiments with several other types of plant cell culture media.

The replacement of the Murashige and Skoog medium by several further types of plant cell culture media (Gamborg also called medium B5, modified Heller, modified Skoog, cf Plant Tissue Culture, Theory and Practice, S. S. Bhojwani and M. K. Razdaw, Elsevier 1983), using otherwise unchanged reaction conditions (cf Example 2a), leads also to a significant increase of the content of irones, see Table II.

TABLE II

| | Variation of the medium | | | |
|---|---|---|---|---|
| | Gamborg | Modified* Heller | Modified** Skoog | Murashige and Skoog |
| mg of irones/kg of dry-weighed rhizomes | 760 | 360 | 630 | 685 |

*Modified Heller: Heller medium with Morel Vitamins (Wetmore R. H., Am. J. Bot., 38 (1951), 141–143; 2–4D (2,4-dichlorophenylacetic acid) (1 mg/ml).
**Modified Skoog: Murashige and Skoog medium with Morel Vitamins, 2–4D (1 mg/liter), kinetin (1 mg/liter).

The strain Serratia liquefaciens used in the Examples was deposited as S.1.1.v under the number I-780 on July 12, 1988 at the Institut Pasteur, Collection Nationale de Cultures de Microorganismes (C.N.C.M.), 25, rue de Docteur Roux 75724- Paris Cedex 15.

EXAMPLE 3

Production of gamma-irone by treatment of iris rhizomes with several other bacterial strains.

Fresh rhizomes (batch I, Example 2) are treated as in Example 2a for one week using one of the following bacteria:

| | |
|---|---|
| Enterbacteriaceae | *Enterobacter cloacae** |
| | *Escherichia coli*** |
| Pseudomonaceae | *Pseudomonas fluorescens** |
| | *Pseudomonas maltophilia* (A.T.C.C. 17866) |

*Isolated from iris rhizomes (procedure for the isolation as in Example 1, note 2), the particular strain of *E. cloacae* was deposited as *E. cloacae* 1 under the number I-779 on July 12, 1988 at the C.N.C.M.
**Strain 54127, subcultured from the collection of the "Unite de Bacteries de l'Institut Pasteur" and supplied by Dr. C. Michel, Laboratoire d'Ichtyopathologie, INRA, Route de Thivernal, 78850 Thiverval-Grignon. The strain has been redeposited as *E. coli* 2 under the number I-794 on July 28, 1988 at the C.N.C.M. I-779, I-780 and I-794 are Budapest deposits.

After incubation, both the rhizomes and the corresponding medium are extracted and analyzed as described in Example 1a. The results, expressed in mg of irones/kg of dry-weighed rhizomes are given in Table III.

TABLE III

| | Influence of strains | | | |
|---|---|---|---|---|
| | *Enterobacter cloacae* | *Escherichia coli* | *Pseudomonas fluorescens* | *Pseudomonas maltophilia* |
| mg of irones/kg of dry-weighed rhizomes | 1073 | 535 | 187 | 174 |

EXAMPLE 4

Production of gamma-irone by treatment of other substrates derived from *Iris pallida* with Serratia liquefaciens in liquid medium.

a) Plant cell culture of Iris pallida.

Callus cultures of Iris pallida have been initiated on Murashige and Skoog medium (cf Example 1, note 1) and on Gamborg medium (cf Example 2b) according to a classical procedure (Plant Tissue, Theory and Practice, S. S. Bhojwani and M. K. Razdaw, Elsevier (1983)). The two strains I1 and I2 of Iris cell cultures are maintained on Petri dishes containing 45ml of semi-solid Murashige and Skoog medium and are subcultured monthly on fresh medium. These strains are transferred to a liquid medium (Murashige and Skoog or Gamborg without Agar), maintained on a gyratory shaker (26° C., 100 revolutions/minute, 15 days), filtered on a nylon cloth (pore size 50mm) and subcultured every two weeks on fresh medium. Once the cultures are two weeks old, 5g of fresh-weighed cells are placed in 250ml Erlenmeyer flasks containing 100ml of Murashige and Skoog medium and 10ml of nutrient broth (cf Example 1). Each flask, except those used for the control experiments, is inoculated with 0.5ml of a 24 hours old culture of Serratia liquefaciens. They are then incubated on a gyratory shaker (100 revolutions/minute) at 25° C. during two weeks. At the end of this period both the biomass and the medium are extracted and analyzed as described in Example 1. The results expressed in mg of irones/kg of dry-weighed iris cells are given in Table IV.

TABLE IV

| | Iris cell strain I1 | Iris cell strain I2 |
|---|---|---|
| Treated iris cells | 35 | 160 |
| Control experiment | 0 | 0 | b) Treatment of iris wastes.

These wastes are the residues recovered after the industrial hydrodistillation of powdered iris rhizomes. These wastes are treated, as described in Example 2a, with Serratia liquefaciens. In Table V, the results of the analysis of the treated wastes (mg of gamma-irone/kg of wastes) are compared to those of the control experiment (without bacteria).

TABLE V

| | Control experiment | Treatment with *Serratia liquefaciens* | |
|---|---|---|---|
| | C | T | T/C |
| mg of gamma-irone/ kg of waste | 40 | 102 | 2.6 | c) Treatment of iris extracts.

A crude extract of iris rhizomes (from Batch II, see Example 2) was prepared as follows: finely divided rhizomes (1000g) are extracted twice with 1000ml of methanol under agitation for 4 hours. After filtration, the combined methanolic solutions are concentrated.

A 5g sample of this resulting crude extract is dissolved in methanol (10ml) and portions of this solution (0.5ml), sterilized by microfiltration (Sartorius NMLPF 0.22mm membrane; SARL, BP 27, 11 avenue du ler mai, 91122 Palaisean cedex) are added to Erlenmeyer flasks, each of them containing 100ml of sterile Murashige and Skoog medium and 10ml of sterile nutrient broth. After inoculation with 0.5ml of a 24 hours old culture (nutrient broth, 25° C., gyratory shaker) of Serratia liquefaciens, the flasks are incubated for 7 days. The total biomass is extracted and analyzed as described in Example 1. The results are listed in Table VI.

TABLE VI

| | Control experiment | Treatment with *Serratia liquefaciens* |
|---|---|---|
| mg of irones/ liter culture | 0.17 | 0.45 |

EXAMPLE 5

Production of gamma-irone by treatment of fresh iris rhizomes with a culture of Serratia liquefaciens in bioreactors under batch or double phase separating conditions.

a) Production of irones in a batch stirred bioreactor.

Powdered rhizomes (150g) from Batch II (see Example 2) and three liters of Murashige and Skoog medium are placed in a 5 liter bioreactor and autoclaved at 115° C. during 25 minutes After addition of 300ml of sterilized nutrient broth (see Example 1), the mixture is inoculated with 50ml of a bacterial suspension of Serratia liquefaciens (cf Example 1). The culture is maintained at 25° C. for 8 days under mechanical stirring (100 revolutions/minute) and an aeration of 0.2 V.V.M. (0.2 volumes air/volume of medium/minute.). Samples of 100ml are taken after 1, 2 and 5 days for analysis. A control experiment without bacterial inoculation (i.e., medium not inoculated with Serr. liq.) is run in an Erlenmeyer flask on a gyratory shaker under otherwise identical conditions. Extraction of the samples furnished the results as given in Table VII (analysis carried out as described in Example 1).

TABLE VII

| Sampled after: | mg of irones/kg of dry-weighed rhizomes |
|---|---|
| 24 h | 411 |
| 48 h | 404 |
| 120 h | 370 |
| 120 h (control) | 160 | b) Production of gamma-irone under double phase separating conditions.

Operating conditions for keeping separated the rhizomes from the bacteria by a dialysis membrane:

Small pieces of peeled iris rhizomes (Batch I, Example 2) are placed in 10cm dialysis tubes (Prolabo [BP 369; 75525 Paris Cedex]; Ref. 24132, 5g/tube) and both ends of the tubes are closed with special plastic joints (Spectra [Spectrum Medical Industry Inc. 60916 Terminal Annex, Los Angeles, California 960]; ref. 132736). Each one of the so prepared dialysis tubes is placed in a 500ml flask containing 250ml of Murashige and Skoog medium and the whole apparatus is autoclaved at 115° C. during 20 minutes. After cooling and addition of nutrient broth (30ml) each flask, except those used for the control experiments, is inoculated with 1.5ml of a bacterial suspension of Serratia liquefaciens (cf Example 1). After one week of incubation at 25° C. on a gyratory shaker (100 revolutions/minute), both the total biomass (rhizomes extraction tube and bacterial extraction flask) and the medium (extraction tube and extraction flask) are extracted and analyzed as described in Example 2a. The results are shown in Table VIII.

TABLE VIII

| | Control experiment* | Treatment with Serratia liquefaciens | |
|---|---|---|---|
| | (C) | (T) | (T/C) |
| mg of irones/ kg of dry-weighed rhizomes | 63 | 1074 | 17 |

*Murashige and Skoog medium and nutrient broth is not inoculated.

EXAMPLE 6

Production of gamma-irone by treatment of iris rhizomes with an enzyme fraction, as represented by a bacterial cell free medium.

The process is carried out in two steps:

first step: preparation of a "conditioned medium", i.e., incubation of iris rhizomes with Serratia liquefaciens in a liquid plant cell culture medium and nutrient broth and separation of the residual rhizomes. This medium now contains the enzymes.

second step: incubation of iris rhizomes with the "conditioned medium."

a) First step:

Dry rhizomes (batch II, Example 2) are incubated with Serr. liq. as in Example 2a (4×250ml Erlenmeyer flasks) for one week except that the Murashige and Skoog medium is replaced by a buffered plant cell culture medium which is prepared in the following way:

a biological buffer (M.E.S., i.e., 2-(N-morpholino)ethanesulfonic acid, Sigma ref.: M 8250) is added to non-sterilized Murashige and Skoog medium to obtain a concentration of 50 mmoles/liter and the pH is adjusted to a value of 6 using a 3N potassium hydroxide solution. The mixture is autoclaved at 115° C during 20 minutes or sterilized by microfiltration (Millipore membrane, 0.2mm).

After one week of incubation, no bacterial viability was observed any more in the four flasks. At the end of this period the residual rhizomes were separated from the medium by filtration on a nylon cloth of 50mm porosity. Hereinafter the thus obtained filtrate (medium and dead bacterial cells and enzymes) will be referred to as "conditioned medium."

b) Second step

The "conditioned medium" (100ml) is centrifuged at a temperature of 0°-4°C. under 12000 g during 10 minutes or under 43140 g during 20 minutes in order to separate first the dead bacterial cells from the medium.

The supernatant is used to incubate 5g of iris rhizomes (batch II of Example 2, sterilized by autoclaving at 120° C. during 30 minutes) in a 250ml Erlenmeyer flask, on a gyratory shaker (100 revolutions/minute, at 25° C. during one week.

The centrifugation residue is mixed with 100ml of the previously prepared buffered Murashige and Skoog medium wherein the pH had been adjusted to 5 and then used as above to incubate 5g of iris rhizomes.

Control experiments using the "conditioned medium" with and without rhizomes were run under otherwise identical conditions.

Extraction of the samples and analysis as described in Example 1 afforded the results as given in Table IX.

TABLE IX

| | mg of irones/kg of dry-weighed rhizomes |
|---|---|
| Control experiments (a) | |
| Conditioned medium | 29 |
| Conditioned medium + rhizomes | 868 |
| Experimental cultures (b) | |
| Supernatant + rhizomes | 772 |
| Centrifugation residue + rhizomes | 174 |
| Centrifugation 43140 g/10 minutes | |
| Supernatant + rhizomes | 703 |
| Centrifugation residue + rhizomes | 229 |

Conclusions a) This Example establishes once more the formation of gamma-irone ex (from non-mature) rhizomes in a liquid medium (see also Example 2).

b) This Example establishes the fact that the major part of the active enzymes are soluble in water and are extra-cellular enzymes.

The strains I-780, I-779, I-794 will be available to the public on Feb. 5, 1990.

EXAMPLE 7

Production of gamma-irone v̇ treatment of iris rhizomes with an enzyme fraction.

The procedure is as described in Example 6, except that the "conditioned medium" prepared in the first step of Example 6 is replaced by a so-called "preculture" (without using rhizomes) obtained in the following way:

A quantity of 100ml of a buffered plant cell culture medium prepared as described in Example 6 and 10ml of nutrient broth (see Example 1) are added to each flask of a group of 4×250ml Erlenmeyer flasks. Each of the flasks is inoculated with Serratia liquefaciens and incubated as in Example 2. After an incubation period of 24 hours this culture, called preculture, is used for the second step, instead of the "conditioned medium", as described and used in Example 6. The results are as given in Table X.

TABLE X

|  | mg of irones/kg of dry-weighed rhizomes |
|---|---|
| Control experiment | 236 |
| Experimental culture |  |
| Centrifugation 43140 g/20 minutes |  |
| Supernatant and rhizomes | 615 |

The invention being thus described, it will be obvious that the same may be varied in many ways. Such variations are not to be regarded as a departure from the spirit and scope of the invention and all such modifications are intended to be included within the scope of the following claims.

We claim:

1. A process for the preparation of gamma-irone by bioconversion comprising treating an iris rhizome substrate selected from the group consisting of iris rhizomes, iris rhizome parts, iris rhizome extracts, iris rhizome extraction wastes, plant cell cultures of iris rhizomes, and mixtures thereof, with a bacteria selected from the genera group consisting of Enterobacteriacea, Pseudomonacea, and mixtures thereof, in the presence of a plant cell culture medium, and recovering the gamma-irone.

2. The process according to claim 1, wherein the bacteria is selected from the group consisting of *Serratia liquefaciens, Enterobacter cloacae, Escherichia coli, Pseudomonas fluoresecens, Pseudomonas maltophilia*, and mixtures thereof.

3. The process according to claim 2, wherein the bacteria is isolated from an iris rhizome.

4. The process according to claim 1, wherein the iris rhizome substrate is derived from an iris plant selected from the group consisting of *Iris pallida, Iris fluorentina, Iris germanica*, Iris of Verona, and mixtures thereof.

5. The process according to claim 1, wherein the iris rhizome substrate is fresh.

6. The process according to claim 1, wherein the iris rhizome substrate is an iris rhizome extract.

7. The process according to claim 1, wherein the iris rhizome substrate is an iris rhizome extraction waste.

8. The process according to claim 1, wherein the iris rhizome substrate is a plant cell culture of an iris rhizome.

9. The process according to claim 1, wherein the plant cell culture medium is selected from the group consisting of the Murashige and Skoog medium, the Gamborg medium, the modified Heller and the modified Skoog medium, and mixtures thereof.

10. The process according to claim 1, wherein the plant cell culture medium is a semi-solid medium.

11. The process according to claim 1, wherein the plant cell culture medium is a liquid medium.

12. The process according to claim 1, wherein the bioconversion process is carried out in a bioreactor.

13. The process according to claim 1, wherein cis-alpha-irone, trans-alpha-irone, and beta-irone are also prepared.

14. The process according to claim 1, wherein the bioconversion process is conducted at about ambient temperature.

15. The process according to claim 1, wherein the bioconversion process is carried out for a period of time from about 1 to about 20 days.

16. The process according to claim 1, wherein the gamma-irone is isolated by extraction or distillation.

17. The process according to claim 9, wherein the plant cell culture medium further comprises a nutrient broth.

18. The process according to claim 17, wherein the ratio of plant cell culture medium to the total medium of plant cell culture medium and nutrient broth is from about 0.5:1 to about 0.95:1.

19. The process according to claim 1, wherein the range of the ratio by weight of iris rhizome substrate to medium is from about 1:20 to about 2:1.

20. The process according to claim 1, wherein the bacteria selected from the group consisting of Enterobacteriacea, Pseudomonacea, and mixtures thereof, is extracted with water to obtain an aqueous extract of bacteria, and the iris rhizome substrate is treated with the aqueous extract of bacteria in the presence of a plant cell culture medium, and the gamma-irone is recovered.

* * * * *